(12) United States Patent
Parker et al.

(10) Patent No.: US 8,154,173 B2
(45) Date of Patent: Apr. 10, 2012

(54) MECHANICALLY AMPLIFIED PIEZOELECTRIC TRANSDUCER

(75) Inventors: John Parker, Roseville (AU); Hans Jaeger, Thunstetten (CH); Christian M. Peclat, Neuchatel (CH)

(73) Assignee: Cochlear Limited, Macquarie University, NSW (AU)

( * ) Notice: Subject to any disclaimer, the term of this patent is extended or adjusted under 35 U.S.C. 154(b) by 436 days.

(21) Appl. No.: 12/168,572

(22) Filed: Jul. 7, 2008

(65) Prior Publication Data

US 2009/0247811 A1    Oct. 1, 2009

Related U.S. Application Data

(60) Provisional application No. 61/041,185, filed on Mar. 31, 2008.

(51) Int. Cl.
*H01L 41/08* (2006.01)
(52) U.S. Cl. ............................ 310/328; 310/354
(58) Field of Classification Search .................. 310/328, 310/354
See application file for complete search history.

(56) References Cited

U.S. PATENT DOCUMENTS

| | | | |
|---|---|---|---|
| 2,045,403 A | 6/1936 | Nicholides | |
| 2,045,404 A | 6/1936 | Nicholides | |
| 2,045,427 A | 6/1936 | White | |
| 2,239,550 A | 4/1941 | Cubert | |
| 4,612,915 A | 9/1986 | Hough et al. | |
| 4,937,489 A * | 6/1990 | Hattori et al. | |
| 4,952,835 A | 8/1990 | Stahlhuth | |
| 4,964,106 A | 10/1990 | Bromfield | |
| 5,286,199 A | 2/1994 | Kipke | |
| 5,444,324 A | 8/1995 | Priest et al. | |
| 5,589,725 A | 12/1996 | Haertling | |
| 5,772,575 A | 6/1998 | Lesinski et al. | |
| 6,273,681 B1 * | 8/2001 | Yamakawa et al. | 416/23 |
| 6,294,859 B1 * | 9/2001 | Jaenker | 310/328 |
| 6,371,415 B1 | 4/2002 | Lorkowski et al. | |
| 6,411,009 B2 | 6/2002 | Jaenker | |
| 6,463,157 B1 | 10/2002 | May | |
| 6,927,528 B2 | 8/2005 | Barillot et al. | |
| 6,994,110 B2 | 2/2006 | Barillot et al. | |
| 7,026,746 B2 * | 4/2006 | Audren et al. | 310/328 |
| 7,045,932 B2 * | 5/2006 | Xu et al. | 310/323.17 |
| 0,041,595 A1 | 2/2007 | Carazo et al. | |
| 7,378,783 B2 * | 5/2008 | Pelrine et al. | 310/311 |

(Continued)

FOREIGN PATENT DOCUMENTS

DE    19643180    4/1997

(Continued)

OTHER PUBLICATIONS

Sichel, et al. "New Approach for Implantable Hearing Aids: A Feasibility Study" Ann Otol Rhinol Laryngol. 113:2004, pp. 936-940.

(Continued)

*Primary Examiner* — Thomas M Dougherty
(74) *Attorney, Agent, or Firm* — Kilpatrick, Townsend & Stockton, LLP.

(57) ABSTRACT

A piezoelectric transducer having a component therein for amplifying the deformation of the piezoelectric element so as to increase the available transducer stroke. This amplification of the piezoelectric element may be provided by a mechanical amplifier coupled to the piezoelectric element. The mechanical amplifier is configured to exert a preloading force on the piezoelectric element.

23 Claims, 12 Drawing Sheets

U.S. PATENT DOCUMENTS

| | | | |
|---|---|---|---|
| 0,245,555 A1 | 10/2009 | Parker | |
| 2003/0137218 A1* | 7/2003 | Hermle et al. | 310/328 |
| 2006/0025648 A1 | 2/2006 | Lupin et al. | |
| 2009/0115292 A1* | 5/2009 | Ueda et al. | 310/338 |
| 2009/0245553 A1* | 10/2009 | Parker | 381/326 |
| 2009/0247810 A1* | 10/2009 | Parker et al. | 600/25 |
| 2009/0248085 A1* | 10/2009 | Parker | 606/300 |
| 2009/0248086 A1* | 10/2009 | Parker | 606/300 |

FOREIGN PATENT DOCUMENTS

| | | |
|---|---|---|
| WO | 03001846 | 1/2003 |
| WO | WO 2009/121116 A1 * | 10/2009 |
| WO | WO-2009121104 | 10/2009 |

OTHER PUBLICATIONS

Selection guide for piezo actuators. Cedrat Technologies—Piezo Products Catalogue—Version 3.0—Sep. 2003.

Piezomechanik GmbH. Piezoelectric bending actuators Disk Translators ("bimorphs") Piezoelectric tubes. pp. 1-12.

Janocha, Hartmut, "Actuators: Basics and Applications", 2004, pp. 265-267, Springer-Verlag.

Juuti et al., "Mechanically Amplified large displacement piezoelectric actuators", Sensors and Actuators A, Dec. 22, 2004, vol. 120, pp. 225-231.

Takashi, Oota, Abstract of Japanese Patent Publication No. 59-178986, Patent Abstracts of Japan, Oct. 11, 1984.

Hattori et al., Abstract of Japanese Patent Publication No. 64-073781, Patent Abstracts of Japan, Mar. 20, 1989.

International Preliminary Report on Patentability for PCT/AU2009/000358, dated Oct. 5, 2010, 7 pages.

International Search Report for PCT/AU2009/000358, mailed Jul. 14, 2009, 4 pages.

Written Opinion for PCT/AU2009/000358, mailed Jul. 14, 2009, 6 pages.

International Preliminary Report on Patentability for PCT/AU2009/000372, dated Oct. 5, 2010, 8 pages.

International Search Report for PCT/AU2009/000372, mailed Jun. 29, 2009, 3 pages.

Written Opinion for PCT/AU2009/000372, mailed Jun. 29, 2009, 7 pages.

Yutaka, Abe, Abstract of Japanese Patent Publication No. 01-290272, Patent Abstracts of Japan, Nov. 22, 1989.

Zhou et al., "Analysis of a diamond-shaped mechanical amplifier for a piezo actuator", Int J Adv Manuf Technol, Mar. 18, 2006, vol. 32, pp. 1-7.

Piezomechanik Gmbh, "Piezoelectric bending actuators, Disk translators ("bimorphs"), Piezoelectric tubes," Mar. 2002, pp. 1-12.

* cited by examiner

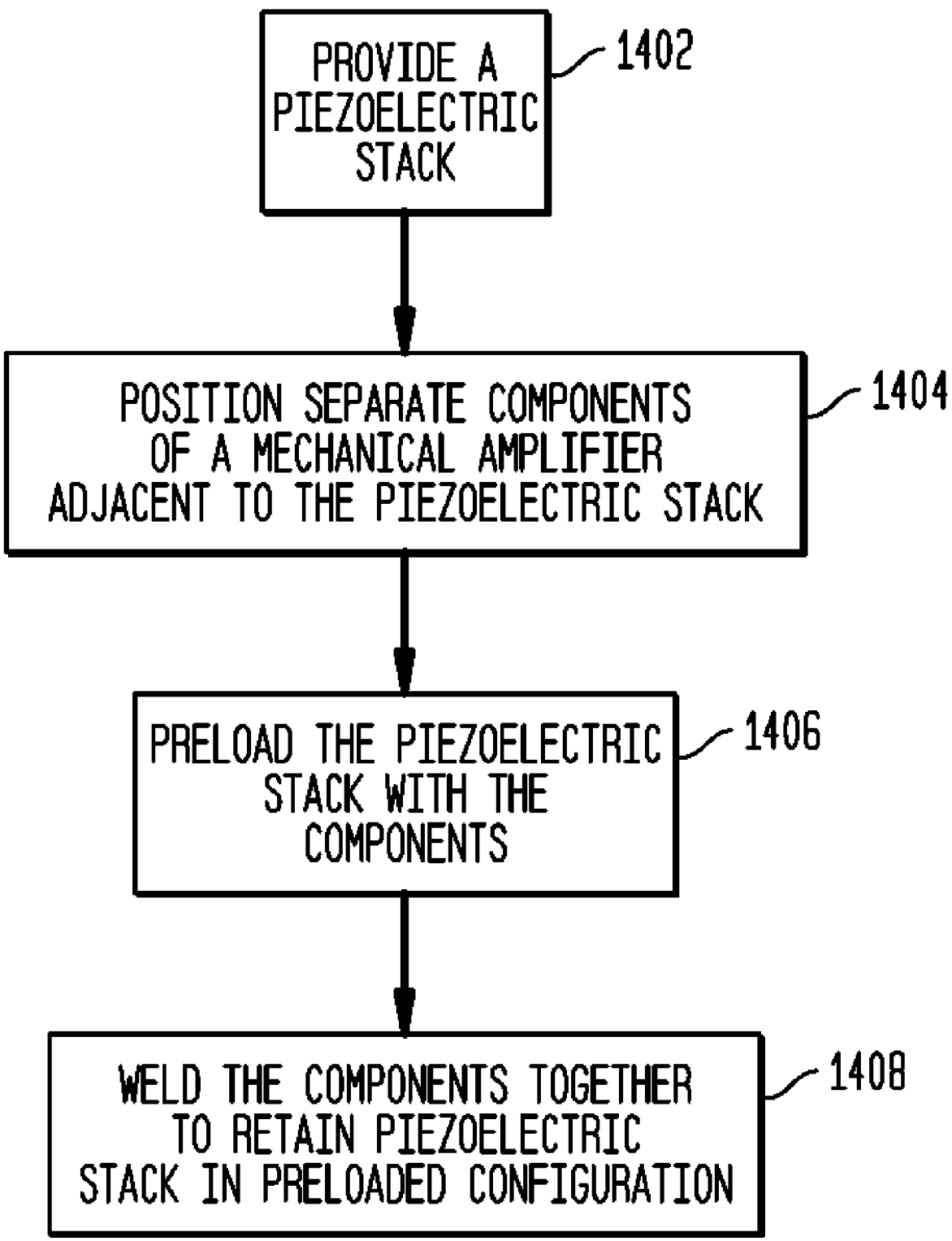

MECHANICALLY AMPLIFIED PIEZOELECTRIC TRANSDUCER

CROSS-REFERENCE TO RELATED APPLICATIONS

The present application claims the benefit of U.S. Provisional Patent Application 61/041,185; filed Mar. 31, 2008, which is hereby incorporated by reference herein.

BACKGROUND

1. Field of the Invention

The present invention is generally directed to a bone conduction device, and more particularly, to a mechanically amplified piezoelectric transducer.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to bypass the mechanisms of the ear. More specifically, an electrical stimulus is provided via the electrode array directly to the cochlea nerve, thereby causing a hearing sensation.

Conductive hearing loss occurs when the normal mechanical pathways to provide sound to hair cells in the cochlea are impeded, for example, by damage to the ossicular chain to ear canal. However, individuals who suffer from conductive hearing loss may still have some form of residual hearing because the hair cells in the cochlea are may remain undamaged.

Individuals who suffer from conductive hearing loss are typically not candidates for a cochlear implant due to the irreversible nature of the cochlear implant. Specifically, insertion of the electrode array into a recipient's cochlea exposes the recipient to risk of the destruction of the majority of hair cells within the cochlea. The destruction of the cochlea hair cells results in the loss of all residual hearing by the recipient.

Rather, individuals suffering from conductive hearing loss typically receive an acoustic hearing aid, referred to as a hearing aid herein. Hearing aids rely on principles of air conduction to transmit acoustic signals through the outer and middle ears to the cochlea. In particular, a hearing aid typically uses an arrangement positioned in the recipient's ear canal to amplify a sound received by the outer ear of the recipient. This amplified sound reaches the cochlea and causes motion of the cochlea fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of medical conditions such as Treacher Collins syndrome or Microtia. Furthermore, hearing aids are typically unsuitable for individuals who suffer from single-sided deafness (total hearing loss only in one ear). Cross aids have been developed for single sided deaf individuals. These devices receive the sound from the deaf side with one hearing aid and present this signal (either via a direct electrical connection or wirelessly) to a hearing aid which is worn on the opposite side. The disadvantage of this technology is the need for the individual to wear two hearing aids and suffer the complications of hearing aid use.

When an individual having fully functional hearing receives an input sound, the sound is transmitted to the cochlea via two primary mechanisms: air conduction and bone conduction. As noted above, hearing aids rely primarily on the principles of air conduction. In contrast, other devices, referred to as bone conduction devices, rely predominantly on vibration of the bones of the recipients skull to provide acoustic signals to the cochlea.

Those individuals who cannot derive suitable benefit from hearing aids may benefit from bone conduction devices. Bone conduction devices function by converting a received sound into a mechanical vibration representative of the received sound. This vibration is then transferred to the bone structure of the skull, causing vibration of the recipient's skull. This skull vibration results in motion of the fluid of the cochlea. Hair cells inside the cochlea are responsive to this motion of the cochlea fluid, thereby generate nerve impulses resulting in the perception of the received sound.

A known alternative to a normal air conduction aid is a bone conduction hearing aid which uses a hearing aid to drive a vibrator which is pushed against the skull via a mechanism, such as glasses or wire hoops. These devices are generally uncomfortable to wear and, for some recipients, are incapable of generating sufficient vibration to accurately present certain received sounds to a recipient.

SUMMARY

In one aspect of the invention, a mechanical amplifier configured to amplify a deformation of a piezoelectric stack and configured to exert a preloading force on said stack, is provided. The mechanical amplifier comprises: first endplate positioned parallel to and adjoining a first end of said stack; a second endplate positioned parallel to and adjacent a second end of said stack; a pair of opposing hinge arms extending from said first endplate to said second endplate about opposing sides of said stack; and a piston configured to extend from said second endplate to said second end of said so as to exert an adjustable preload force on said stack.

In a second aspect of the present invention, a mechanical amplifier configured to amplify a deformation of a piezoelectric stack and configured to exert a preloading force on said stack, is provided. The mechanical amplifier comprises: a first endplate positioned parallel to and adjoining a first end of said stack; a pair of opposing hinge arms extending from said first endplate about opposing sides of said stack; and a second endplate positioned parallel to and adjoining a second end of said stack configured to be adjustable along an axis parallel to a longitudinal axis of said stack so as to vary said preloading force exerted on said stack, and wherein said opposing arms are configured to be secured to said second endplate when said second endplate has been adjusted along said axis so as to exert a desired preloading force on said stack.

In a third aspect of the present invention, a mechanical amplifier configured to amplify a deformation of a piezoelectric stack and configured to exert a preloading force on said stack, is provided. The mechanical amplifier comprises: a first endplate positioned parallel to and adjoining a first end of said stack; a second endplate positioned parallel to and adjoining a second end of said stack; a pair of opposing hinge arms extending from said first endplate to said second endplate about opposing sides of said stack; wherein said first endplate, said second endplate and said hinge arms collectively comprise two or more separate components configured to be positioned about said stack so as to directly exert a desired preloading force thereon, and wherein said two or more components are secured in said position to exert said desired preloading force via welds between said two or more components.

BRIEF DESCRIPTION OF THE DRAWINGS

Illustrative embodiments of the present invention are described herein with reference to the accompanying drawings, in which:

FIG. 14 is a flowchart illustrating the manufacturing of a mechanically amplified piezoelectric element in accordance with embodiments of the present invention.

DETAILED DESCRIPTION

Figure 1:
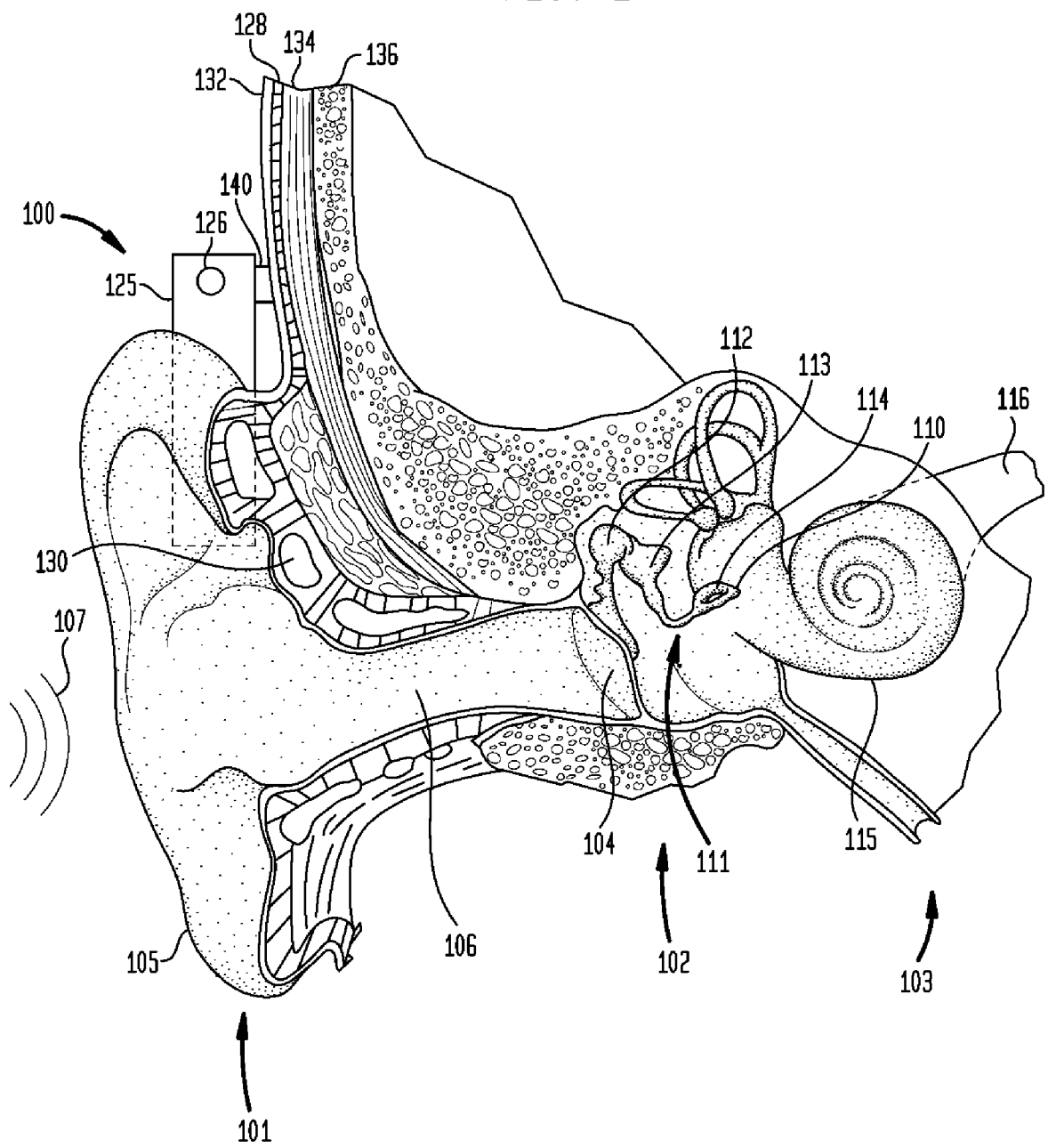
FIG. 1 is a perspective view of an exemplary medical device, namely a bone conduction device, in which embodiments of the present invention may be advantageously implemented.

The output stroke of the transducer (sometimes referred to herein as the "transducer stroke") is utilized to generate a mechanical force output by the transducer. The maximum available transducer stroke is based on the possible deformation of the piezoelectric element. The amount of deformation of a piezoelectric element in response to an applied electrical signal depends on, for example, material properties of the element, orientation of the electric field with respect to the polarization direction of the element, geometry of the element, etc.

Embodiments of the present invention are generally directed to amplifying the deformation of piezoelectric element so as to increase the available transducer stroke, thereby increasing the maximum force that may be output by the transducer. This amplification of the piezoelectric element may be provided by a mechanical amplifier coupled to the piezoelectric element.

Due to the fact that piezoelectric elements are structurally weak when placed under tension, mechanical amplifiers in accordance with the present invention are configured to exert a force (pre-load) on the piezoelectric element that eliminates tensile force on the piezoelectric element. This allows the voltage to swing through zero. The exertion of this force on the element is sometimes referred to herein as preloading, and the force is referred to as a preloading force. As described below, the magnitude of the preloading force may vary depending on the desired application of the transducer.

In some embodiments of the present invention, a mechanical amplifier configured to amplify a deformation of a piezoelectric element, as well as to exert a desired preloading force on the element comprises first and second endplates, and a pair of opposing hinge arms. The first endplate is positioned parallel to and adjoining a first end of the element, while the second endplate is positioned parallel to and adjacent the opposite end of the element. The opposing hinge arms extend from the first endplate to the second endplate about opposing sides of the piezoelectric element. The amplifier has a piston which extends from the second endplate to the adjacent end of the element. The piston may be adjusted along a longitudinal axis parallel to a longitudinal axis so as to exert controllable preloading force on the piezoelectric element.

In other embodiments of the present invention, the mechanical amplifier comprises first endplate positioned parallel to and adjoining a first end of the element, a pair of opposing hinge arms extending from the first endplate about the element, and a second endplate. The second endplate is positioned parallel to and adjoining a second end of the element. The second endplate is adjustable along an axis parallel to a longitudinal axis of the stack so as to vary a preloading force exerted on the stack. The opposing arms are configured to be secured to the second endplate when the second endplate via welds once the endplate has been adjusted along the axis so as to exert the desired preloading force on the element.

In alternative embodiments, the mechanical amplifier comprises first and second endplates and a pair of opposing hinge arms extending from the first endplate to the second endplate about opposing sides of the element. The first endplate, the second endplate and the hinge arms collectively comprise two or more separate components configured to be positioned about the element so as to directly exert a desired preloading force thereon. The two or more components are secured to one another in the position to exert the desired preloading force via welds.

In one such embodiment in which the first endplate, the second endplate and the hinge arms collectively comprise two or more separate components, the first endplate and a first one of the hinge arms comprise a first unitary structure. Similarly, in this embodiment, the second endplate and a second one of the hinge arms comprise a second unitary structure. The first endplate is configured to be welded to the end of the second arm opposing the second endplate and the second endplate is configured to be welded to the end of the first arm opposing the first endplate. Following the welding, the first and second structures collectively exert the desired preloading force on the stack.

In one other such embodiment in which the first endplate, the second endplate and the hinge arms collectively comprise two or more separate components, the amplifier comprises first and second unitary hook-shaped structures. A first unitary hook-shaped structure comprises the first endplate, a substantial portion of the first hinge arm, and at least a portion of the second hinge arm. A second hook-shaped structure comprises the second endplate, a substantial portion of the second hinge arm, and at least a portion of the first hinge arm. The ends of the substantial portions of the first and second arms are configured to be welded to one to the remaining portions of the arms, respectively, and wherein following the welding the structures collectively exert the desired preloading force on the components.

In still other embodiments the mechanical amplifier comprises four separate components. A first component includes the first endplate and at least a portion of each of the hinge arms, while a second component includes the second endplate and at least a portion of each of the hinge arms. The amplifier also includes first linking region configured to extend between the portions of the first hinge arm, and a second linking region configured to extend between the portions of the second hinge arm. In these embodiments of the present invention, the first and second components are configured to be positioned such that each endplate is adjoining an end of the piezoelectric element. The first and components are moved relative to one another so as to exert a force on the piezoelectric element that eliminates tensile force on the piezoelectric element. When a desired force is asserted on the piezoelectric stack, the ends of each of the linking regions are configured to be welded to the ends of the hinge arm portions of the first and second components, respectively.

Various devices make use of piezoelectric transducers. Embodiments of the present invention will be discussed herein with reference to one exemplary such device which makes use of a piezoelectric transducer, namely a bone conduction device. Bone conduction devices convert a received acoustic sound signal into a mechanical force for delivery to a recipient's skull which results in a sound perception by the recipient. Bone conduction device includes a sound input component, such as microphone, to receive the acoustic sound signal, an electronics module configured to generate an electrical signal representing the acoustic sound signal, and a piezoelectric transducer to convert the electrical signal into the mechanical force for delivery to the recipient's skull.

FIG. 1 is a perspective view of embodiments of a bone conduction device 100 in which embodiments of the present invention may be advantageously implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates cochlear hair cells (not shown). Cochlear hair cells come in two anatomically and functionally distinct types: the outer and inner hair cells. Activation of one or more types of these hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient.

In the embodiments illustrated in FIG. 1, bone conduction device 100 comprises a housing 125 having a microphone 126 positioned therein or thereon. Housing 125 is coupled to the body of the recipient via coupling 140. As described below, bone conduction device 100 may comprise a sound processor, a transducer, transducer drive components and/or various other electronic circuits/devices.

In accordance with embodiments of the present invention, an anchor system (not shown) may be implanted in the recipient. As described below, the anchor system may be fixed to bone 136. In various embodiments, the anchor system may be implanted under skin 132 within muscle 134 and/or fat 128. In certain embodiments, a coupling 140 attaches device 100 to the anchor system.

Figure 2A:
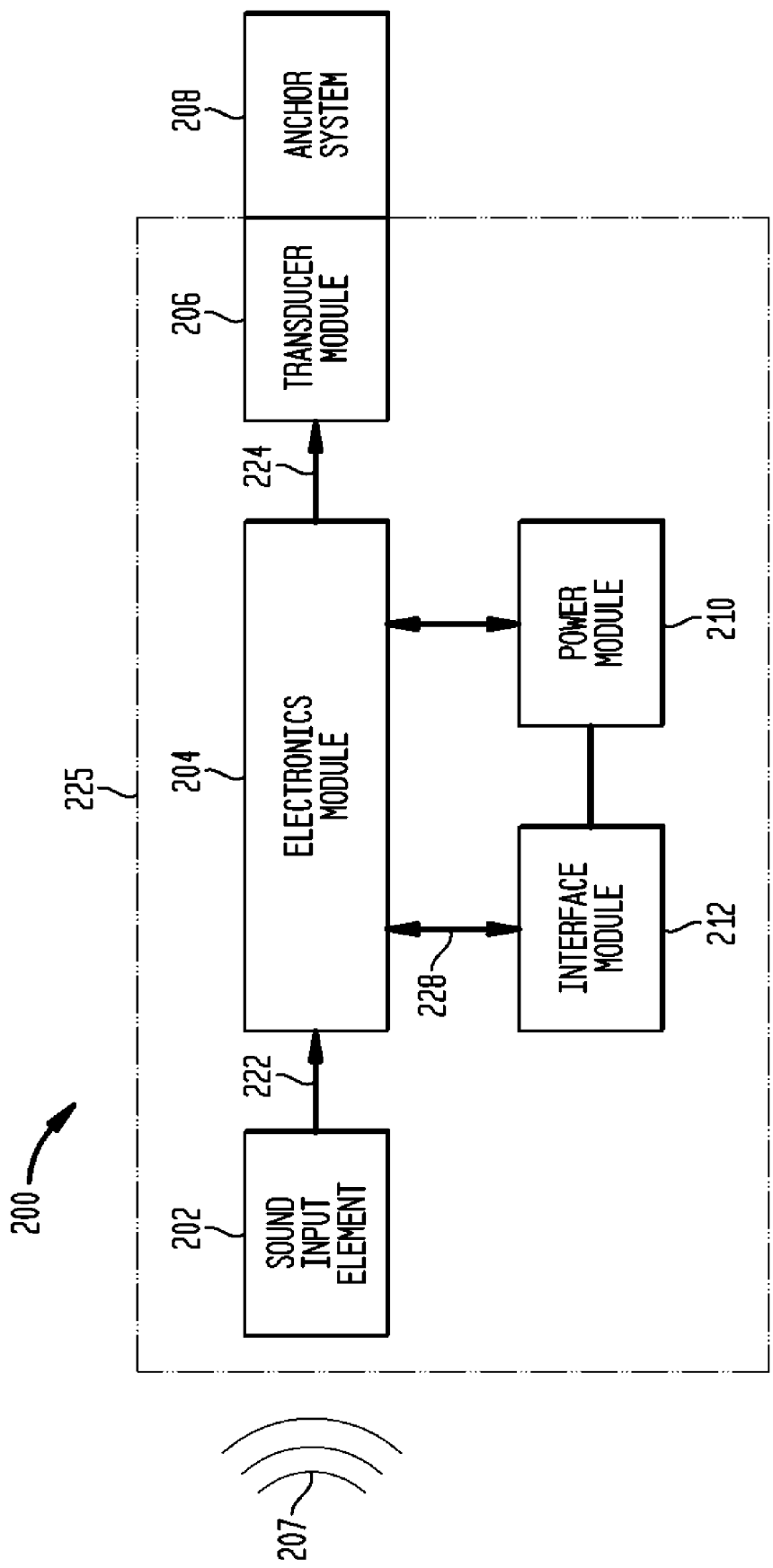
FIG. 2A is a high-level functional block diagram of a bone conduction device, such as the bone conduction device of FIG. 1.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, a transducer 206 receives adjusted electrical signal 224 and generates a mechanical output force that is delivered to the skull of the recipient via an anchor system 208 coupled to bone conduction device 200. Delivery of this output force causes one or more of motion or vibration of the recipient's skull, thereby activating the hair cells in the cochlea via cochlea fluid motion.

FIG. 2A also illustrates a power module 210. Power module 210 provides electrical power to one or more components of bone conduction device 200. For ease of illustration, power module 210 has been shown connected only to interface module 212 and electronics module 204. However, it should be appreciated that power module 210 may be used to supply power to any electrically powered circuits/components of bone conduction device 200.

Bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2A, sound pickup device 202, electronics module 204, transducer 206, power module 210 and interface module 212 have all been shown as integrated in a single housing, referred to as housing 225.

However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

Figure 2B:
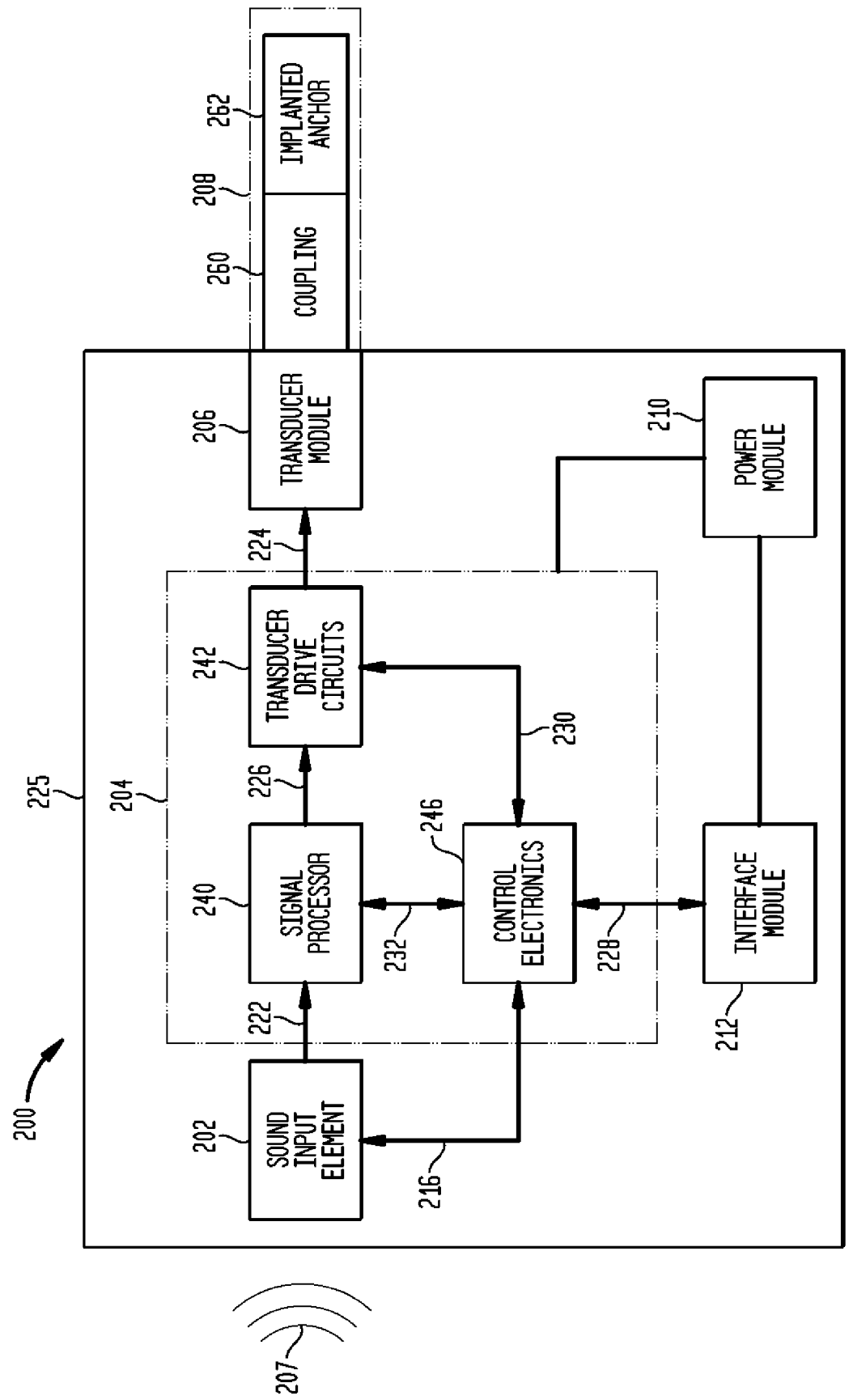
FIG. 2B is detailed functional block diagram of the bone conduction device illustrated in FIG. 2A.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 226A is provided to transducer drive components 242. Transducer drive components 242 output a drive signal 224B, to transducer 206. Based on drive signal 224B, transducer 206 provides the output force to the skull of the recipient.

For ease of description the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, anchor system 208 comprises a coupling 260 and an implanted anchor 262. Coupling 260 may be attached to one or more of transducer 206 or housing 225. For example, in certain embodiments, coupling 260 is attached to transducer 206 and vibration is applied directly thereto. In other embodiments, coupling 260 is attached to housing 225 and vibration is applied from transducer 206 through housing 225.

As shown in FIG. 2B, coupling 260 is coupled to an anchor implanted in the recipient, referred to as implanted anchor 262. As explained with reference to FIG. 3, implanted anchor 262 provides an element that transfers the vibration from coupling 260 to the skull of the recipient.

As noted above, a recipient may control various functions of the device via interface module 212. Interface module 212 includes one or more components that allow the recipient to provide inputs to, or receive information from, elements of bone conduction device 200.

As shown, control electronics 246 may be connected to one or more of interface module 212, sound pickup device 202, sound processor 240 and/or transducer drive components 242. In embodiments of the present invention, based on inputs received at interface module 212, control electronics 246 may provide instructions to, or request information from, other components of bone conduction device 200. In certain embodiments, in the absence of user inputs, control electronics 246 control the operation of bone conduction device 200.

Figure 3:
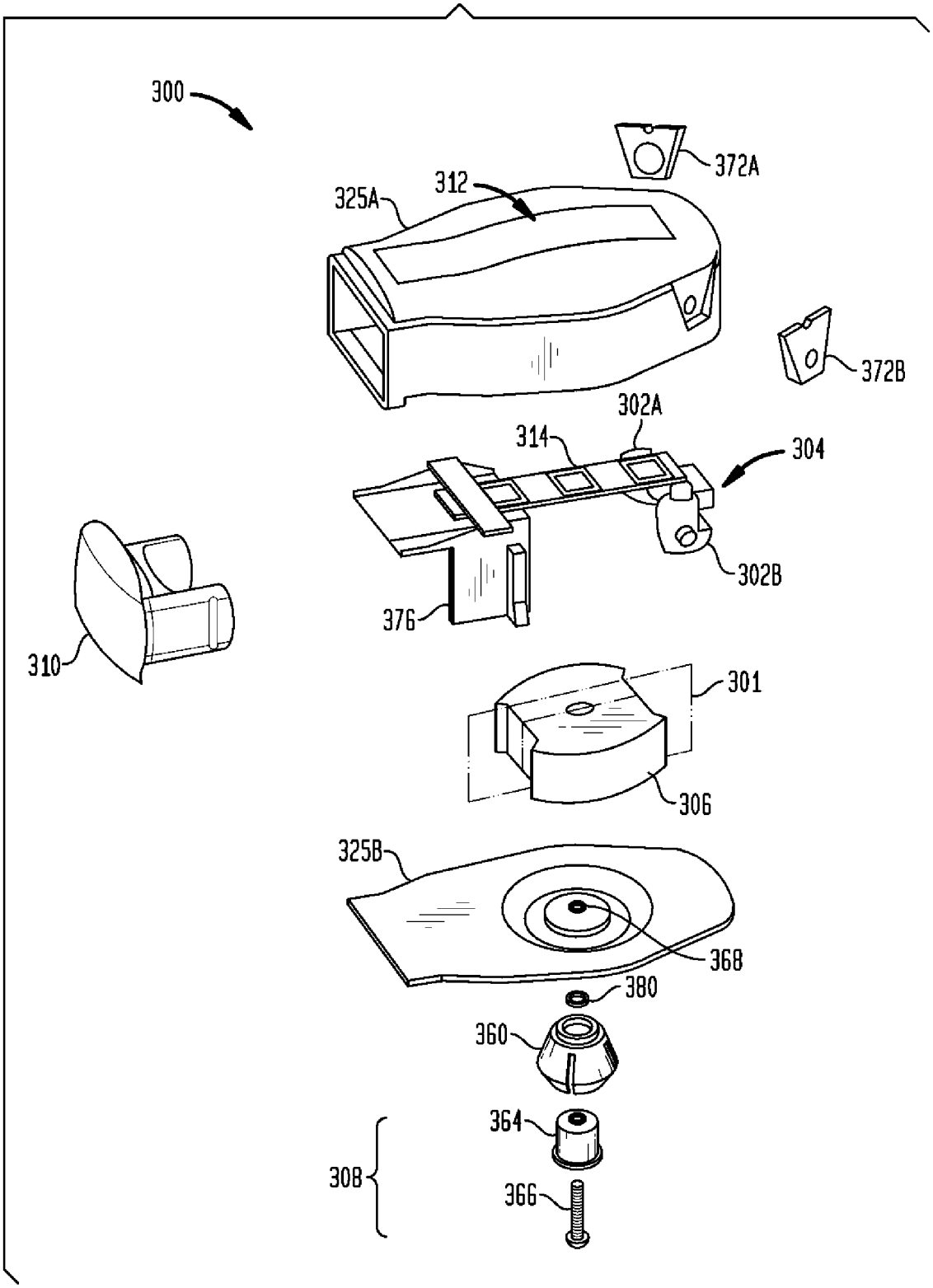
FIG. 3 is an exploded view of an embodiment of a bone conduction device in accordance with one embodiment of FIG. 2B.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, included within electronics module 304 are a sound processor, transducer drive components and control electronics. For ease of illustration, these components have not been illustrated in FIG. 3.

In the illustrated embodiment, electronics module 304 includes a printed circuit board 314 (PCB) to electrically connect and mechanically support the components of electronics module 304. Attached to PCB 314 are one or more sound input elements, shown as microphones 302 to receive a sound.

In the illustrated embodiment, bone conduction device 300 further comprises battery shoe 310 for supplying power to components of device 300. Battery shoe 310 may include one or more batteries. In certain embodiments, PCB 314 is attached to a connector 376. Connector 376 is configured to mate with battery shoe 310. In certain embodiments, connector 376 and battery shoe 310 may be releasably snap-locked to one another. Furthermore, in such embodiments, one or more battery connects (not shown) are disposed in connector 376 to electrically connect battery shoe 310 with electronics module 304.

In the embodiment illustrated in FIG. 3, bone conduction device 300 further includes a two-part housing 325, comprising first housing portion 325A and second housing portion 325B. Housing portions 325 are configured to mate with one another to substantially seal bone conduction device 300.

In the embodiment of FIG. 3, first housing portion 325A has an opening therein for receiving battery shoe 310. In such embodiments, battery shoe protrudes through first housing portion 325A and may be removed or inserted by the recipient. Also in the illustrated embodiment, microphone covers 372 are releasably attached to first housing portion 325A. Microphone covers 372 provide a barrier over microphones 302 to protect microphones 302 from dust, dirt or other debris.

Bone conduction device 300 further includes an embodiment of interface module 212, referred to herein as interface module 312. Interface module 312 is configured to provide or receive user inputs from the recipient.

Also as shown in FIG. 3, bone conduction device 300 comprises an embodiment of transducer 206, referred to as transducer 306. Transducer 306 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360 and implanted anchor 362. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 362. Implanted anchor 362 comprises a bone screw 366 implanted in the skull of the recipient and an abutment 364. In an implanted configuration, screw 366 protrudes from the recipient's skull through the skin. Abutment 364 is attached to screw 366 above the recipient's skin. In other embodiments, abutment 364 and screw 366 may be integrated into a single implantable component. Coupling 360 is configured to be releasably attached to abutment 364 to create a vibratory pathway between transducer 306 and the skull of the recipient.

In alternative embodiments of the present invention, bone conduction device 300 may comprise one or more additional sound input element. For example, bone conduction device 300 may comprises an electrical input 316. In such embodiments, the electrical input is configured to connect device 300 to external equipment and receive an electrical sound signal directly therefrom. Electrical input 316 may permit bone conduction device 300 to be connected to, for example, FM hearing systems, MP3 players, televisions, mobile phones, etc.

In still other embodiments, a further sound input element in the form of a telecoil 318 may be integrated in, or connected to, bone conduction device 300. Telecoil 318 permits bone conduction device 300 to receive input signals from, for example, a telephone or other similar device.

Figure 4:
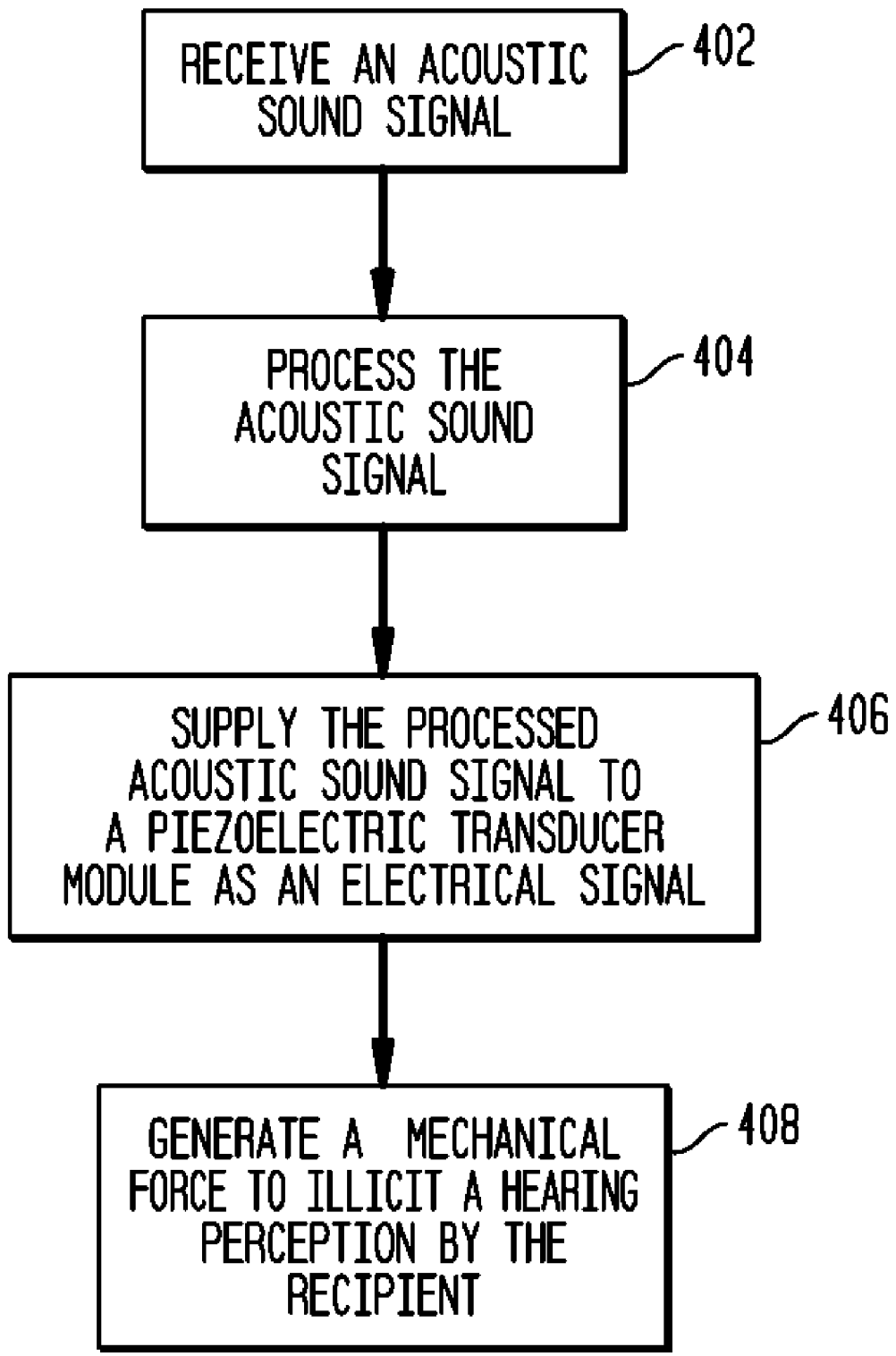
FIG. 4 is a flowchart illustrating the conversion of an input sound into skull vibration in accordance with embodiments of the present invention.

FIG. 4 illustrates the conversion of an input acoustic sound signal into a mechanical force for delivery to the recipient's skull in accordance with embodiments of bone conduction device 300. At block 402, bone conduction device 300 receives an acoustic sound signal. In certain embodiments, the acoustic sound signal is received via microphones 302. In other embodiments, the input sound is received via an electrical input. In still other embodiments, a telecoil integrated in, or connected to, bone conduction device 300 may be used to receive the acoustic sound signal.

At block 404, the acoustic sound signal received by bone conduction device 300 is processed by the speech processor in electronics module 304. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by bone conduction device 300.

At block 406, the processed sound signal is provided to transducer 306 as an electrical signal. At block 408, transducer 306 converts the electrical signal into a mechanical force configured to be delivered to the recipient's skull via anchor system 308 so as to illicit a hearing perception of the acoustic sound signal.

Figure 5:
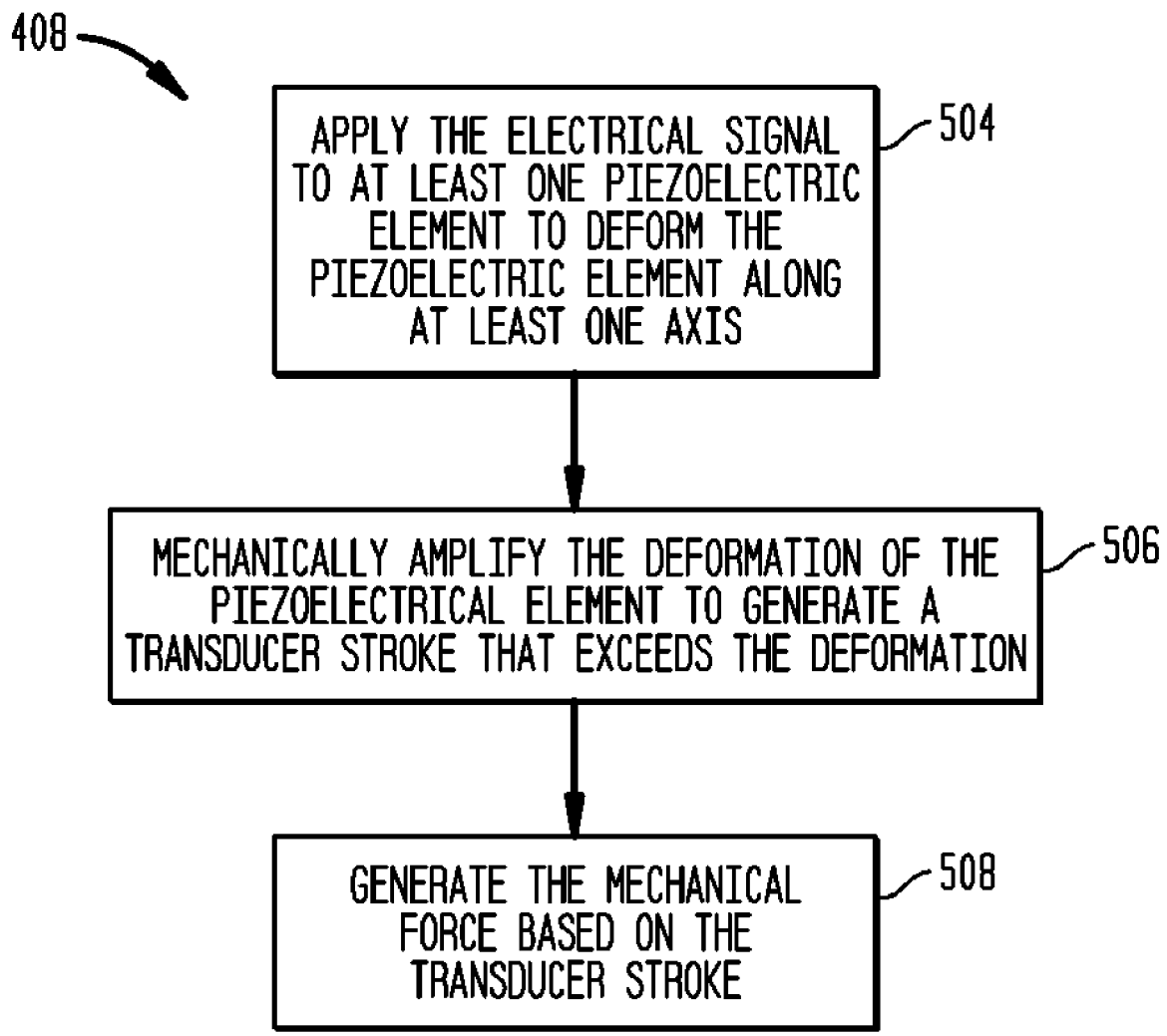
FIG. 5 is a flowchart illustrating the generation of mechanical skull in accordance with one embodiment of block 408 of FIG. 4.

FIG. 5 illustrates one embodiment of block 408 of FIG. 4 in accordance with certain embodiments of the present invention. At block 504, the electrical signal is applied to at least one piezoelectric element. As explained above, the piezoelectric element is configured to deform in response to the application of the electrical signal thereto. Piezoelectric elements that may be used in embodiments of the present invention may comprise, for example, piezoelectric crystals, piezoelectric ceramics, or some other material exhibiting a deformation in response to an applied electrical signal. Exemplary piezoelectric crystals include quartz ($SiO_2$), Berlinite ($AlPO_4$), Gallium orthophosphate ($GaPO_4$) and Tourmaline. Exemplary piezoelectric ceramics include barium titanate ($BaTiO_3O$), lead zirconate titanate (PZT), or zirconium (Zr).

Some piezoelectric materials, such as PZT, are polarized materials. When an electric field is applied across these materials, the polarized molecules align themselves with the electric field, resulting in induced dipoles within the molecular or crystal structure of the material. This alignment of molecules causes the deformation of the material under an applied electric field.

Returning to the embodiments illustrated in FIG. 5, at block 506 the deformation of the piezoelectric element is mechanically amplified to generate a transducer stroke that exceeds the deformation of the piezoelectric element. As explained in detail below, a mechanical amplifier is provided to generate the transducer stroke based on the deformation of the piezoelectric element. At block 508, the mechanical force for delivery to the recipient's skull is generated based on the transducer stroke applied to the attached mass 560. The force applied is simply the mass times the acceleration which is applied by the transducer.

Figure 6:
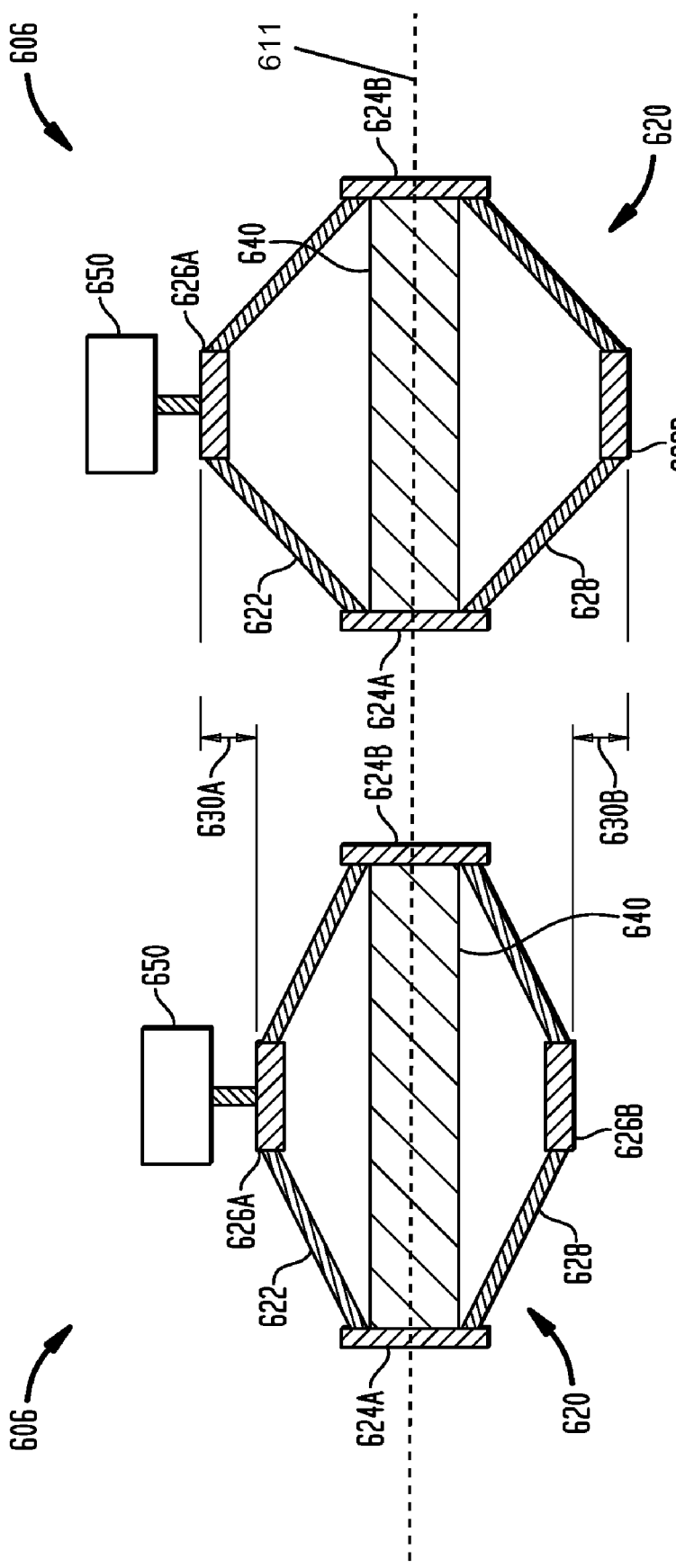
FIG. 6A is a simplified schematic diagram illustrating embodiments of transducer 306 of FIG. 3.
FIG. 6B is a simplified schematic diagram illustrating embodiments of transducer 306 of FIG. 3.

FIGS. 6A and 6B are simplified schematic diagrams illustrating embodiments of transducer 306 of FIG. 3, referred to herein as transducer 606. As shown, transducer 606 comprises a mechanical amplifier in accordance with embodiments of the present invention, illustrated as mechanical amplifier 620, a piezoelectric element 640 and a mass 650.

In the embodiments of FIGS. 6A and 6B, mechanical amplifier 620 converts a deformation of piezoelectric element 640 into a mechanical deflection of one or portions of mechanical amplifier 620. The collective deflection of these portions exceeds the magnitude of the deformation of piezoelectric element 640. In these embodiments, the output stroke for transducer 606 comprises this collective deflection of the portions of mechanical amplifier 620. As discussed in detail below, mechanical amplifier 620 is configured to exert a pre-loading force on piezoelectric element 640.

In the illustrative embodiments of FIGS. 6A and 6B, piezoelectric element 640 comprises a plurality of layers of stacked piezoelectric material, referred to herein as a piezoelectric stack 640. For example, in some embodiments, piezoelectric stack 640 comprises a plurality of stacked PZT layers.

In the exemplary embodiments of FIGS. 6A and 6B, mechanical amplifier 620 comprises two endplates 624 each coupled to a separate end of piezoelectric stack 640. Mechanical amplifier 620 further comprises opposing hinge arms 622, 628, extending between endplates 624. Arms 622 and 628 are positioned on opposing sides of piezoelectric element 640. In the embodiments of FIGS. 6A and 6B, each opposing arm 622, 628, and piezoelectric stack 640 define a frusto-conical shape there between. In these embodiments, each arm 622, 628 has a portion 626 spaced from piezoelectric element 640 by a distance that exceeds the remainder of each of arms 622, 628.

FIG. 6A illustrates the configuration of transducer 606 prior to application of an application signal to piezoelectric stack 640, while FIG. 6B illustrates the configuration of transducer 606 following application of the electrical signal to stack 640. Prior to application of the electrical signal, portions 626 of arms 622, 628 are each spaced a first distance from piezoelectric element 640. Following application of the electrical signal, piezoelectric stack 640 deforms along an axis extending there through substantially parallel to portions 626. This axis is illustrated as axis 611. As shown, piezoelectric stack 640 deforms by contracting along axis 611. This contraction of piezoelectric stack 640 along axis 611 causes portions 626 to deflect outwards from piezoelectric stack 640 along an axis substantially perpendicular to the axis of contraction, illustrated as axis 613 in FIGS. 6A and 6B. The magnitude of the deflection of each portion 626 is illustrated in FIGS. 6A and 6B as deflection 630.

In these embodiments, the magnitude of the collective deflection of portions 626 is referred to as the stroke of transducer 606. Due to the configuration of opposing arms 622, 628, the magnitude of the collective deflections 630 exceeds the magnitude of the contraction of piezoelectric stack 640 along axis 611. As would be appreciated, the larger the collective deflection of portions 626, the greater the stroke of transducer 606.

As noted above, transducer 606 includes a mass 650. When portions 626 deflect away from piezoelectric element 640, mass 650 is caused to move in proportion to the transducer stroke. This motion of mass 650 results in the generation of a mechanical force which may be output by transducer 606. In the embodiment of FIG. 6B, the generated mechanical force is illustrated by force arrow 625.

In the illustrated embodiment, hinge arm 622, 628 are utilized to output the mechanical force to, for example, a coupling described above with reference to FIG. 3. Hinge arms 622, 638 a sufficiently rigid material so as to output the mechanical force, but have dimensions, thickness and or other material properties that permit the deflection of portions 626 discussed above. Hinge arms 622, 628, and mechanical amplifier in general, may comprise a variety of materials. In certain embodiments, mechanical amplifier 620 is tungsten. In other embodiments, mechanical amplifier 620 is stainless steel.

As discussed in more detail below, mechanical amplifier 620 may comprise a single unitary piece. In other embodiments, mechanical amplifier 620 may comprise two or more components welded to one another.

Figure 7:
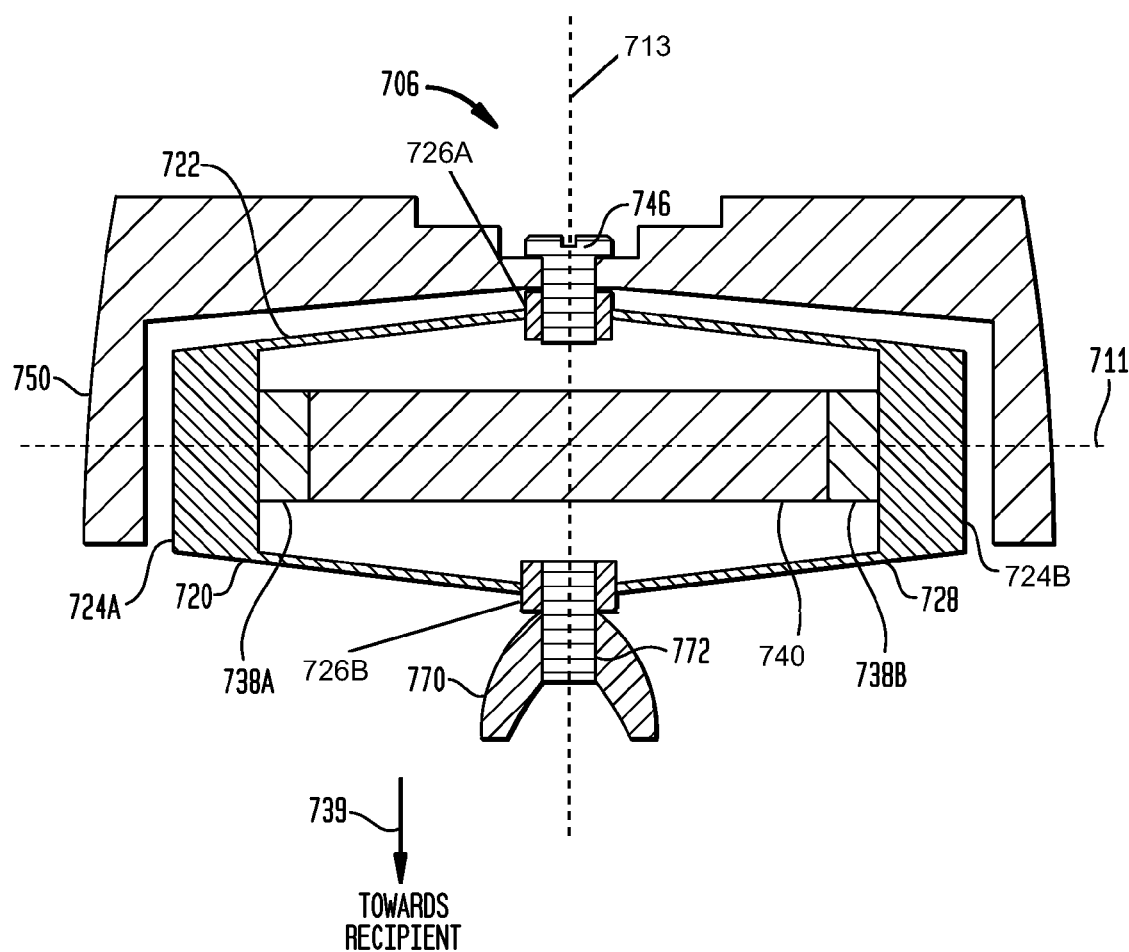
FIG. 7 is a cross-sectional view of one embodiment of transducer 306 of FIG. 3 along cross-sectional plane 201.

FIG. 7 is a cross-sectional view of one exemplary embodiment of transducer 306, taken along cross-sectional plane 301 of FIG. 3, referred to herein as transducer 706. Transducer 706 is substantially similar to transducer 606 of FIGS. 6A and 6B. Transducer 706 comprises a piezoelectric element 740, mechanical amplifier 720 and mass 750. Mechanical amplifier similarly comprises endplates 724, arms 722, 728 and portions 726. In the illustrative embodiment, endplate 724B is attached to an end of piezoelectric stack 740. Endplate 724A is coupled to piezoelectric stack 740 via a preloading element 738. Preloading in accordance with embodiments of the present invention is discussed below in more detail. For example, as discussed below, mechanical amplifier 720 may be designed to exert the desired preloading force on piezoelectric stack 740 without preloading element 738.

Mass 750 may be attached to portion 726A of arm 722. As shown in FIG. 7, portion 726A is attached to mass 750 via attachment screw 746. Portion 726B of arm 628 is attached to a coupling 770 via coupling screw 772. As explained above with reference to FIG. 3, a coupling, such as coupling 770, may be attached to an anchor implanted in the recipient.

As noted, when an electrical signal is applied to piezoelectric stack 740, stack 740 deforms along axis 711 and portions 726 deflect away from piezoelectric stack 740 along axis 713. In this illustrative embodiment, axis 713 is substantially perpendicular to the recipient's skull. As such, portion 726B deflects toward the recipient, while portion 726A deflects away from the recipient. As noted above, the magnitude of this collective deflection, referred to as the stroke of transducer 706, causes motion of mass 750. This motion in turn generates a mechanical force. This mechanical force may be output to coupling 770 and relayed to the anchor implanted in the recipient.

Figure 8:
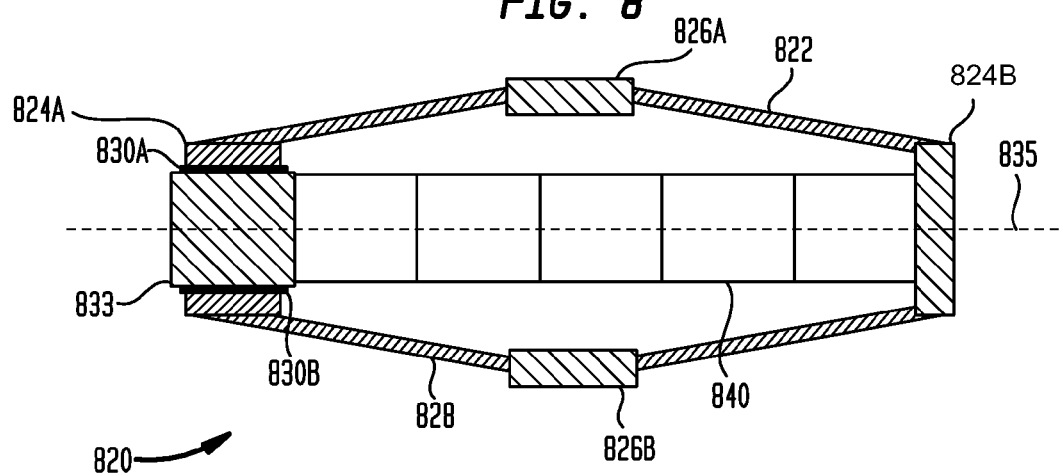
FIG. 8 is a simplified schematic diagram illustrating embodiments of a piezoelectric transducer having a welded amplifier in accordance with embodiments of the present invention.

FIG. 8 schematically illustrates one embodiment of a mechanical amplifier in accordance with aspects of the present invention, referred to as mechanical amplifier 820. As shown, mechanical amplifier 820 comprises a first endplate 824A, a second endplate 824B, opposing hinge arms 822, 828, and a piston 833.

As discussed above, when an electrical signal is applied to a piezoelectric stack, such as stack 840, stack 840 deforms by contracting along at least one axis. In FIG. 8, this axis of contraction is illustrated as axis 835. This contraction of stack 840, causes hinge arms 822, 828 to bend, thereby deflecting one or more portions of hinge arms 822, 828 outwards from piezoelectric stack 840. In the illustrated embodiments, portions 826 of hinge arms 822, 828 are configured to deflect outward from piezoelectric stack 840. The magnitude of this collective deflection, referred to as the stroke of the transducer, is an amplified representation of the deformation of piezoelectric stack 840.

As described above, a piezoelectric element, such as piezoelectric stack 840, is structurally weak when placed under a tensile force. Furthermore, to operate in an oscillating operation, the force applied to the piezoelectric element by the mechanical amplifier must be such that deformation of the piezoelectric element causes the hinge arms of the mechanical amplifier to bend, as described above. The force which causes bending of the hinge arms is sometimes referred to herein as a desired preloading force.

As such, mechanical amplifier 820 is configured to exert the desired preloading force on piezoelectric stack 820. In the embodiment of FIG. 8, mechanical amplifier 820 includes a piston 833 that is used in conjunction with first endplate 824B to exert a desired preloading force on piezoelectric stack 840.

As shown in FIG. 8, first endplate 824B is positioned parallel to and adjoining a first end of piezoelectric stack 840. Second endplate 824A is positioned parallel to and adjacent the opposite end of piezoelectric stack 840. Second endplate 824A is spaced from stack 840. Opposing hinge arms 822, 828 extend from first endplate 824B to second endplate 824A 824B about opposing sides of piezoelectric stack 840. In the illustrated embodiment, second endplate 824A has an opening therein, and piston 833 extends through the opening Piston 833 may be secured to second endplate 824A via one or more welds 830.

At least a portion of piston 833 extends from second endplate 824A to piezoelectric stack 840 to exert a force on stack 840 in the direction of first endplate 824B. The force applied by piston 833 may be adjusted, thereby varying the preloading force exerted on piezoelectric stack 840 between first endplate 824B and the piston portion. When a desired preloading force has been exerted, piston 833 may be locked in position so as to retain the force on piezoelectric stack 840.

As shown in FIG. 8, endplates 824 and opposing hinge arms 822, 828 may comprise a unitary component. Endplates 824 and opposing hinge arms 822, 828 comprise a unitary component in that these components comprise a structurally singular entity manufactured as a whole that were not attached to one another via, for example, a weld.

Figure 9:
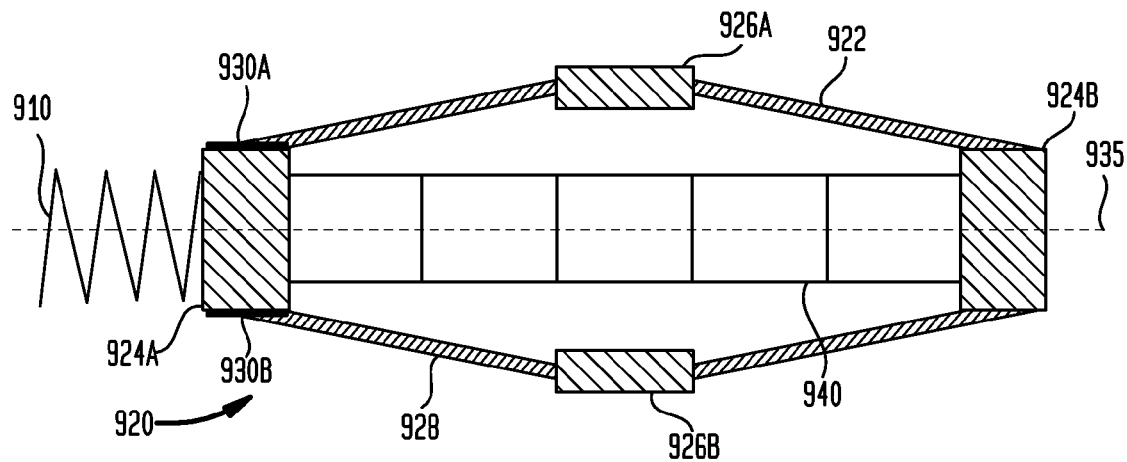
FIG. 9 is a simplified schematic diagram illustrating embodiments of a piezoelectric transducer having a welded amplifier in accordance with embodiments of the present invention.

FIG. 9 schematically illustrates another embodiment of a mechanical amplifier in accordance with aspects of the present invention, referred to as mechanical amplifier 920. As shown, mechanical amplifier 920 comprises first and second endplates 924 and opposing hinge arms 922, 928.

Similar as described above with reference to FIG. 8, when an electrical signal is applied to a piezoelectric stack 940, stack 940 deforms by contracting along at least one axis, illustrated as axis 935. This contraction of stack 940, causes hinge arms 922, 928 to bend, thereby deflecting one or more portions of hinge arms 922, 928 outwards from piezoelectric stack 940. The magnitude of this collective deflection, referred to as the stroke of the transducer, is an amplified representation of the deformation of piezoelectric stack 940.

Also as described above with reference to FIG. 8, for proper amplification of the deformation of piezoelectric stack 940, mechanical amplifier 920 is configured to exert a desired preloading force on piezoelectric stack 920. In the embodiment of FIG. 9, this desired preloading force is exerted by first and second endplates 924.

As shown in FIG. 9, first endplate 924B is positioned parallel to and adjoining a first end of piezoelectric stack 940. Second endplate 924B is positioned parallel to and adjoining the opposite end of piezoelectric stack 940. In these embodiments, second endplate 924A is adjustable along an axis parallel to a longitudinal axis of piezoelectric stack 940, illustrated as axis 935. Adjustment of second endplate 924A along axis 935 varies the preloading force exerted on piezoelectric stack 940. Adjustment of second endplate 924A may be provided, for example, by a spring mechanism 910.

After second endplate 924A has been adjusted such that piezoelectric stack 940 is under a desired preloading force, opposing hinge arms 922, 928 are each configured to be secured to second endplate 924A via welds 930. After hinge arms 922, 928 are secured to second endplate 924A, spring mechanism 910 would be removed.

As shown in FIG. 9, first endplate 924B and hinge arms 922, 928 comprise a unitary component. First endplate 924B and opposing hinge arms 922, 928 comprise a unitary component in that these components comprise a structurally singular entity manufactured as a whole that were not attached to one another via, for example, a weld.

Figure 10:
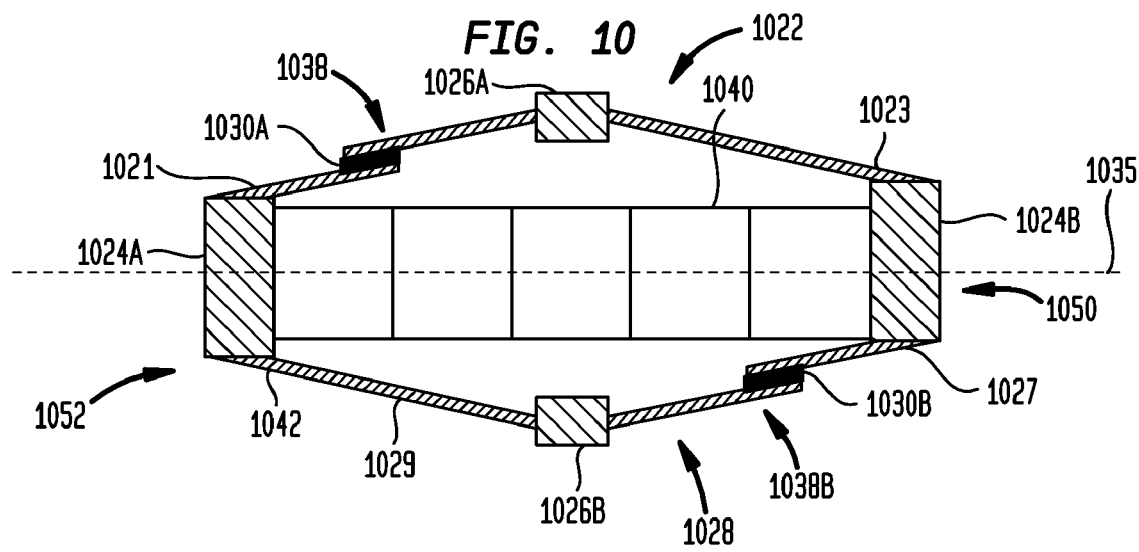
FIG. 10 is a simplified schematic diagram illustrating embodiments of a piezoelectric transducer having a welded amplifier in accordance with embodiments of the present invention.

FIG. 10 schematically illustrates alternative embodiments of a mechanical amplifier in accordance with aspects of the present invention, referred to as mechanical amplifier 1020. As shown, mechanical amplifier 1020 comprises first and second endplates 1024 and opposing hinge arms 1022, 1028.

Similar as described above with reference to FIG. 8, when an electrical signal is applied to a piezoelectric stack 1040, stack 1040 deforms by contracting along at least one axis, illustrated as axis 1035. This contraction of stack 1040, causes hinge arms 1022, 1028 to bend, thereby deflecting one or more portions of hinge arms 1022, 1028 outwards from piezoelectric stack 1040. The magnitude of this collective deflection, referred to as the stroke of the transducer, is an amplified representation of the deformation of piezoelectric stack 1040.

Also as described above with reference to FIG. 8, for proper amplification of the deformation of piezoelectric stack 1040, mechanical amplifier 1020 is configured to exert a desired preloading force on piezoelectric stack 1020. In these exemplary embodiments, first and second endplates 1024 exert the desired preloading force on piezoelectric stack 1040.

As shown in FIG. 10, endplates 1024 and hinge arms 1022, 1028 and collectively comprise two separate components, first unitary structure 1050 and second unitary structure 1052. First and second unitary structures 1050, 1052 each have a substantially hook shape. As shown, first unitary structure 1050 comprises first endplate 1024B, a substantial portion of hinge arm 1022, referred to as substantial portion 1023 and at least a portion of hinge arm 1028, referred to as portion 1027. Similarly, second unitary structure 1052 comprises second endplate 1024A, a substantial portion of hinge arm 1028, referred to as substantial portion 1029 and at least a portion of hinge arm 1022, referred to as portion 1021.

In the illustrated embodiment, first and second structures 1050, 1052 are configured to be positioned about piezoelectric stack 1040. When positioned about piezoelectric stack 1040, first endplate 1024B is positioned parallel to and adjoining a first end of piezoelectric stack 1040, while second endplate 1024A is positioned parallel to and adjoining the opposite end of piezoelectric stack 1040. After endplates 1024 are positioned adjoining opposite ends of piezoelectric stack 1040, first and second structures 1050, 1052, are configured to be moved relative to one another so as to exert a preloading force on piezoelectric stack 1040 between endplates 1024.

When the preloading force exerted on piezoelectric stack 1040 reaches a desired level, first and second structures may be secured to one another via welds 1030. As shown in FIG. 10, the end of substantial portion 1023 of hinge arm 1022 is welded to remaining portion 1021. Similarly, the end of substantial portion 1029 of hinge arm 1028 is welded to remaining portion 1027.

As shown, portions of each hinge arm 1022, 1028 overlap at welding regions 838. However, as described below with reference to FIG. 14, it should be appreciated that in certain embodiments there is no overlap between the portions.

Figure 11:
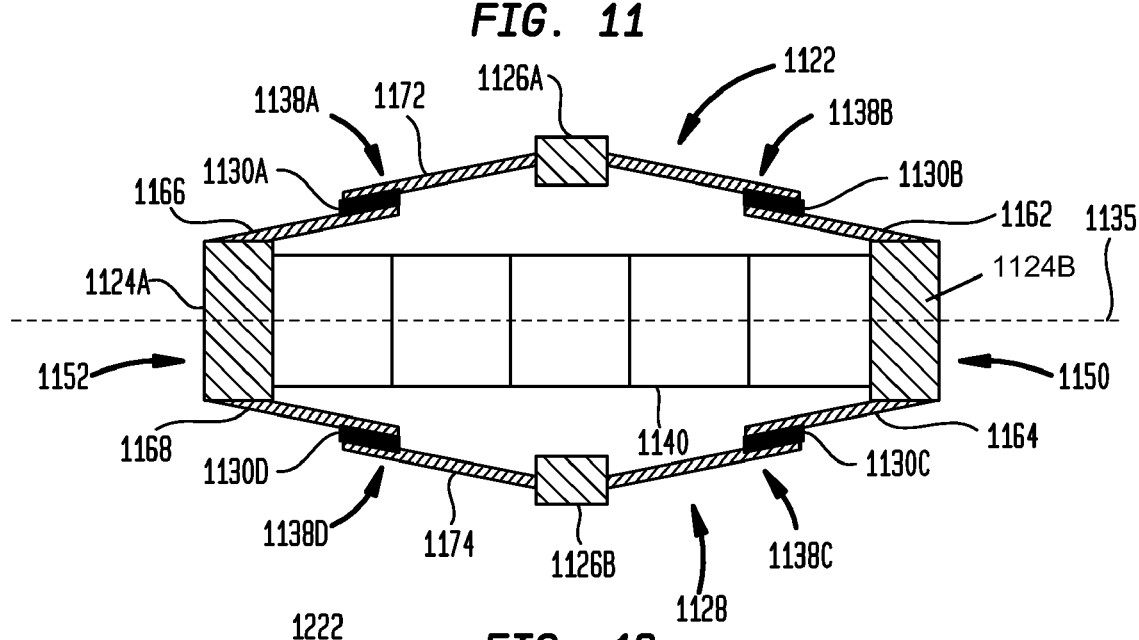
FIG. 11 is a simplified schematic diagram illustrating embodiments of a piezoelectric transducer having a welded amplifier in accordance with embodiments of the present invention.

FIG. 11 schematically illustrates other embodiments of a mechanical amplifier in accordance with aspects of the present invention, referred to as mechanical amplifier 1120. As shown, mechanical amplifier 1120 comprises first and second endplates 1124 and opposing hinge arms 1122, 1128.

Similar as described above with reference to FIG. 8, when an electrical signal is applied to a piezoelectric stack 1140, stack 1140 deforms by contracting along at least one axis, illustrated as axis 1135. This contraction of stack 1140, causes hinge arms 1122, 1128 to bend, thereby deflecting one or more portions of hinge arms 1122, 1128 outwards from piezoelectric stack 1140. The magnitude of this collective deflection, referred to as the stroke of the transducer, is an amplified representation of the deformation of piezoelectric stack 1140.

Also as described above with reference to FIG. 8, for proper amplification of the deformation of piezoelectric stack 1140, mechanical amplifier 1120 is configured to exert a desired preloading force on piezoelectric stack 1120. In these exemplary embodiments, first and second endplates 1124 exert the desired preloading force on piezoelectric stack 1140.

As shown in FIG. 11, endplates 1124 and hinge arms 1122, 1128 and collectively comprise four separate components. A first component 1150 includes first endplate 1124B and at least a portion of each of the hinge arms, portion 1162 of hinge arm 1122 and portion 1164 of hinge arm 1128. A second component 1152 includes second endplate 1124A and at least a portion of each of the hinge arms, portion 1166 of hinge arm 1122 and portion 1168 of hinge arm 1128. The amplifier also includes a first linking region 1172 configured to extend between portions 1162 and 1666 of hinge arm 112, and a second linking region 1174 configured to extend between portions 1164 and 1168 of hinge arm 1128. In these embodiments of the present invention, first and second components 1150, 1152 are configured to be positioned such that each endplate is adjoining an end of piezoelectric stack 1140. First and second components 1150, 1152 are moved relative to one another so as to exert a preloading force on piezoelectric stack 1140. When a desired preloading of piezoelectric stack 1140 is achieved, the ends of each of the linking regions 1172, 1174 are welded to the ends of hinge arm portions of the first and second components, respectively.

As shown, ends of linking regions 1172 and 1174 overlap with hinge arm portions 1162, 1166, and 1164, 1168, respectively, at welding regions 1138. However, as described below with reference to FIG. 14, it should be appreciated that in certain embodiments there is no overlap between the portions.

Figure 12:
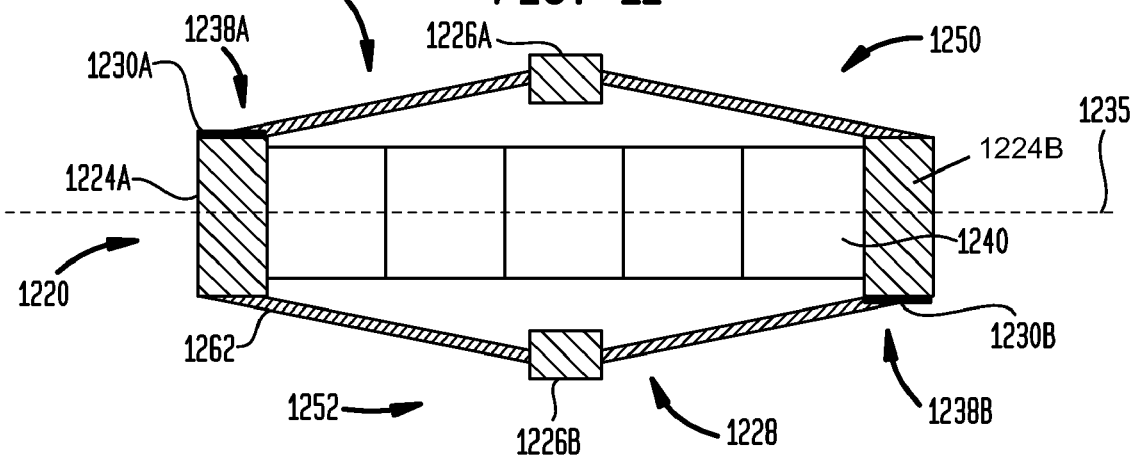
FIG. 12 is a simplified schematic diagram illustrating embodiments of a piezoelectric transducer having a welded amplifier in accordance with embodiments of the present invention.

FIG. 12 schematically illustrates alternative embodiments of a mechanical amplifier in accordance with aspects of the present invention, referred to as mechanical amplifier 1220.

As shown, mechanical amplifier 1220 comprises first and second endplates 1224 and opposing hinge arms 1222, 1228.

Similar as described above with reference to FIG. 8, when an electrical signal is applied to a piezoelectric stack 1240, stack 1240 deforms by contracting along at least one axis, illustrated as axis 1235. This contraction of stack 1240, causes hinge arms 1222, 1228 to bend, thereby deflecting one or more portions of hinge arms 1222, 1228 outwards from piezoelectric stack 1240. The magnitude of this collective deflection, referred to as the stroke of the transducer, is an amplified representation of the deformation of piezoelectric stack 1240.

Also as described above with reference to FIG. 8, for proper amplification of the deformation of piezoelectric stack 1240, mechanical amplifier 1220 is configured to exert a desired preloading force on piezoelectric stack 1220. In these exemplary embodiments, first and second endplates 1224 exert the desired preloading force on piezoelectric stack 1240.

As shown in FIG. 12, endplates 1224 and hinge arms 1222, 1228 collectively comprise two separate components, first unitary structure 1250 and second unitary structure 1252. First unitary structure 1250 comprises first endplate 1224B and hinge arm 1222. Second unitary structure 1252 comprises second endplate 1224A and hinge arm 1228.

In the illustrated embodiment, first and second structures 1250, 1252 are configured to be positioned about piezoelectric stack 1240. When positioned about piezoelectric stack 1240, first endplate 1224B is positioned parallel to and adjoining a first end of piezoelectric stack 1240, while second endplate 1224A is positioned parallel to and adjoining the opposite end of piezoelectric stack 1240. After endplates 1224 are positioned adjoining opposite ends of piezoelectric stack 1240, first and second structures 1250, 1252, are configured to be moved relative to one another so as to exert a force on piezoelectric stack 1240 between endplates 1224.

When the preloading force exerted on piezoelectric stack 1240 reaches a desired level, first and second structures may be secured to one another via welds 1230. As shown in FIG. 12, the 1222 is welded to second endplate 1224A. Similarly, the end hinge arm 1228 is welded to first endplate 1224B.

Figure 13:
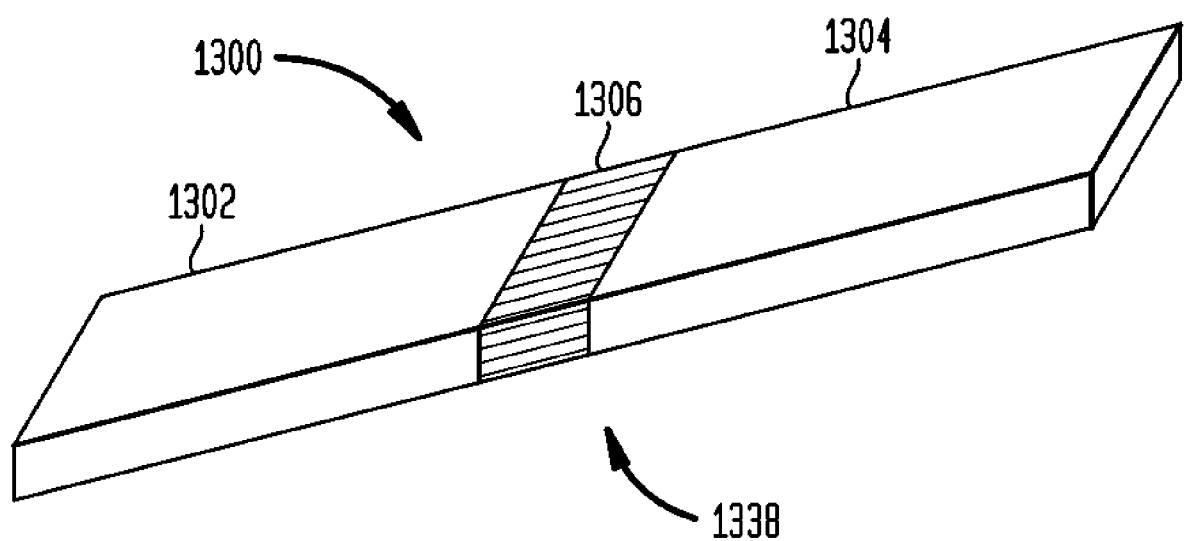
FIG. 13 is an enlarged perspective view illustrating embodiments of a welded region between components of a welded amplifier in accordance with aspects of the present invention.

As illustrated in the embodiments of FIGS. 10 and 11, portions of the hinge arms may overlap at the weld regions. FIG. 13 illustrates an alternative embodiment of these weld regions, shown as weld region 1338, where there is not overlap between portions of a hinge arm. As shown in FIG. 13, at weld region 1338, a weld 1306 secures a first portion 1302 of hinge arm 1300 to a second portion 1304 of hinge arm 1300. First and second regions 1302, 1304 remain substantially aligned with one another and no overlap is necessary.

FIG. 14 is a flowchart illustrating a process for manufacturing a mechanically amplified piezoelectric stack in accordance with embodiments of the present invention. In the illustrated embodiment, at block 1402 a piezoelectric stack is provided. The piezoelectric stack may comprise a pre-manufactured component, or, in alternative embodiments, a piezoelectric stack may be produced using a plurality of piezoelectric layers.

At block 1404, two or more separate components of a mechanical amplifier are positioned adjacent to, and substantially about, the piezoelectric stack. At block 1406, the separate components of the mechanical amplifier are used to preload the piezoelectric stack. As discussed above with reference to FIGS. 8-12, this preloading may be performed in a variety of ways. For example, as described above with reference to FIG. 8, the mechanical amplifier includes a unitary frame comprising first and second endplates and opposing hinge arms, and a piston. The second endplate has a hole therein configured to receive the piston. The unitary frame is positioned about the piezoelectric stack, and piston is positioned though the hole in the second endplate so as to exert a preloading force on the piezoelectric stack. In such embodiments, at block 1408 the piston may be welded to second endplate. In this example, it should be appreciated that the piston may be positioned in, and welded to, the second endplate prior to positioning of the unitary frame about the piezoelectric stack.

Although FIG. 14 has been described herein with reference to the manufacture of one embodiment of a mechanically amplified piezoelectric element of the present invention, namely the embodiment illustrated in FIG. 8, it should be appreciated that the manufacturing process of FIG. 14 may be used for any of the embodiments described herein.

Although the above embodiments have been described herein with reference to a pair of opposing hinge arms positioned around a piezoelectric element, it should be appreciated that alternative embodiments are within the scope of the present invention. For example, in one such alternative embodiment, a mechanical amplifier may comprise a first pair of opposing hinge arms as described above. The mechanical amplifier may further comprise a second pair of opposing hinge arms. These second pair of hinge arms may be positioned, for example, orthogonal to, or parallel to, the first pair of opposing hinge arms. The second pair of opposing hinge arms are similar to the previously described hinge arms and may be positioned, manufactured, etc. in any of the manners described above.

In other embodiments, a hinge arm of the present invention may comprise a split hinge arm. The split hinge arm comprises two portions or arms that extend between endplates of the amplifier. These arms may comprise the same or different material. Likewise, these arms may be substantially parallel to one another, or they may be offset from one another. In operation, two different masses may be coupled to each arm of the split hinge arm so that two different resonant frequencies may be produced.

In other embodiments, a transducer in accordance with embodiments of the present invention may use opposing mechanical amplifiers to amplify the deformation of a piezoelectric element. For example, two mechanical amplifiers, such as those described above, would be used to amplify the deformation of the piezoelectric element. In certain such embodiments, the two mechanical amplifiers would be positioned on opposite sides of the piezoelectric element to amplify the deformation.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A mechanical amplifier configured to amplify a deformation of a piezoelectric stack and configured to exert a preloading force on said stack, the amplifier comprising:

first endplate positioned parallel to and adjoining a first end of said stack;

a second endplate, having an opening therein, positioned parallel to and adjacent a second end of said stack;

a pair of opposing hinge arms extending from said first endplate to said second endplate about opposing sides of said stack; and a piston configured to extend through said opening in said second endplate to said second end of said stack, wherein said piston is adjustable to exert a desired preloading force on said stack.

2. The amplifier of claim 1, wherein each of said hinge arms has a distal portion that is spaced from said stack by a distance that exceeds a distance between said stack and any other portion of said hinge arm.

3. The amplifier of claim 2, wherein each of said hinge arms and said stack have a frusto-conical shape therebetween and wherein said distal portion of each hinge arm defines the apex of said shape.

4. The amplifier of claim 1, wherein a portion of said piston that contacts said stack has a surface area substantially equivalent to the surface area of said second end of said stack.

5. The amplifier of claim 1, wherein a portion of said piston that contacts said stack has a surface area that is larger than the surface area of said second end of said stack.

6. The amplifier of claim 1, wherein said first and second endplates and said hinge arms comprise a unitary structure.

7. The amplifier of claim 1, wherein said first endplate and said hinge arms comprise a unitary structure, and wherein said hinge arms are each secured to said second endplate via a weld.

8. The amplifier of claim 7, wherein said weld is a laser weld.

9. A mechanical amplifier configured to amplify a deformation of a piezoelectric stack, and configured to exert a preloading force on said stack, the amplifier comprising:

a first endplate positioned parallel to and adjoining a first end of said stack;

a pair of opposing hinge arms extending from said first endplate about opposing sides of said stack; and a second endplate positioned parallel to and adjoining a second end of said stack configured to be adjustable along an axis parallel to a longitudinal axis of said stack to exert a desired preloading force on said stack, wherein each of said opposing arms is configured to be secured to said second endplate with the same orientation relative to the stack regardless of said adjusted position of said second endplate.

10. The amplifier of claim 9, wherein each of said hinge arms has a distal portion that is spaced from said stack by a distance that exceeds a distance between said stack and any other portion of said hinge arm.

11. The amplifier of claim 10, wherein each of said hinge arms and said stack have a frusto-conical shape therebetween, and wherein said distal portion of each hinge arm defines the apex of said shape.

12. The amplifier of claim 9, wherein said first endplate and said hinge arms comprise a unitary structure, and wherein said hinge arms are each secured to said second endplate via a weld.

13. The amplifier of claim 12, wherein said weld is a laser weld.

14. A mechanical amplifier configured to amplify a deformation of a piezoelectric stack, and configured to exert a preloading force on said stack, the amplifier comprising:

a first endplate positioned parallel to and adjoining a first end of said stack;

a second endplate positioned parallel to and adjoining a second end of said stack;

a pair of opposing hinge arms extending from said first endplate to said second endplate about opposing sides of said stack;

wherein said first endplate, said second endplate and said hinge arms collectively comprise two or more separate components configured to be positioned about said stack, and wherein a first end of one of said components and a first end of another of said components are configured to be secured to one another at any of a plurality of locations to enable said components to directly exert a desired preloading force on said stack.

15. The amplifier of claim 14, wherein each of said hinge arms has a distal portion that is spaced from said stack by a distance that exceeds a distance between said stack and any other portion of said hinge arm.

16. The amplifier of claim 15, wherein each of said hinge arms and said stack have a frusto-conical shape therebetween, and wherein said distal portion of each hinge arm defines the apex of said shape.

17. The amplifier of claim 14, wherein said welds comprise laser welds.

18. The amplifier of claim 14, wherein said first endplate and a first one of said hinge arms comprise a first unitary structure, and wherein said second endplate and a second one of said hinge arms comprise a second unitary structure, and wherein said first endplate is configured to be welded to the end of said second arm opposing said second endplate, and wherein said second endplate is configured to be welded to the end of said first arm opposing said first endplate, and wherein following said welding, said first and second structures collectively exert said desired preloading force on said stack.

19. The amplifier of claim 14, further comprising:

a first unitary hook-shaped structure comprising said first endplate, a substantial portion of said first hinge arm, and at least a portion of said second hinge arm; and a second hook-shaped structure comprising said second endplate, a substantial portion of said second hinge arm, and at least a portion of said first hinge arm, wherein the ends of said substantial portions of said first and second arms are configured to be welded to one of said remaining portions of said arms, respectively, and wherein following said welding said structures collectively exert said desired preloading force on said components.

20. The amplifier of claim 14, further comprising:

a first component having said first endplate integrated with at least a portion of each of said hinge arms;

a second component having said second endplate integrated with at least a portion of each of said hinge arms;

a first linking region configured to extend between said portions of said first hinge arm; and a second linking region configured to extend between said portions of said second hinge arm, wherein the ends of each of said linking regions are configured to be welded to the ends of said hinge arm portions of said first and second components, respectively, when said components are in a position so as to exert said desired preloading force on said stack.

21. The amplifier of claim 20, wherein said portions of said hinge arms connected to each of said endplates have approximately the same dimensions.

22. The amplifier of claim 9, wherein each of said opposing arms is configured to be directly secured to said second endplate.

23. The amplifier of claim 9, wherein the second endplate is configured to be adjustable along the axis parallel to the longitudinal axis of said stack towards the stack to exert the desired preloading force on said stack.

* * * * *